United States Patent [19]
Miller

[11] Patent Number: 5,940,183
[45] Date of Patent: Aug. 17, 1999

[54] FILTER WHEEL AND METHOD USING FILTERS OF VARYING THICKNESSES

[75] Inventor: Martin Leonard Miller, Rochester, N.Y.

[73] Assignee: Johnson & Johnson Clinical Diagnostics, Inc., Rochester, N.Y.

[21] Appl. No.: 08/873,155

[22] Filed: Jun. 11, 1997

[51] Int. Cl.$^6$ .................................................. G01N 21/25
[52] U.S. Cl. ............................................................. 356/418
[58] Field of Search .................................... 386/418, 419, 386/402–411, 300; 250/226; 359/742, 891, 798, 892

[56] References Cited

U.S. PATENT DOCUMENTS

| | | |
|---|---|---|
| 2,287,322 | 7/1942 | Nelson . |
| 4,979,803 | 12/1990 | McGuckin et al. . |
| 5,298,989 | 3/1994 | Tsukahara et al. . |
| 5,689,341 | 11/1997 | Hayashi ................................. 356/418 |

FOREIGN PATENT DOCUMENTS 3743584  7/1989  Germany .

OTHER PUBLICATIONS

Laser Focus World; "Have You Considered Using Variable Bandpass Filters" Sep. 1989, pp. 1–4.
Translation of German DE 3743584.1, Dec. 22, 1987, Ritzl.

*Primary Examiner*—K. P. Hantis
*Attorney, Agent, or Firm*—Dana M. Schmidt

[57] ABSTRACT

Apparatus for and a method of detection of light transmitted or reflected from a test object using any one of plural filters each with a unique center wavelength. To prevent chromatic aberration in non-collimated light passed through the filters, the thickness of each filter is unique, depending on its center wavelength.

10 Claims, 3 Drawing Sheets

FILTER WHEEL AND METHOD USING FILTERS OF VARYING THICKNESSES

FIELD OF THE INVENTION

This invention relates to a filter assembly and detecting station in an analyzer using such filter assembly, wherein plural filters are used each with a unique center wavelength, as dictated by the various assays that are detectable by the detecting station.

BACKGROUND OF THE INVENTION

Filters in filter wheels have long been known to produce longitudinal chromatic aberrations. That is, the angle of non-collimated light passing through a filter of a specific narrow bandpass, will be altered depending upon the actual wavelengths of the light passing through the filter. This is pursuant to the law of refraction. Because a filter's purpose is to produce differing bandpass wavelengths, one for each filter, in an analyzer reflectometer, for example, the result when using non-collimated light through filters of equal thicknesses is to alter at each filter the focal length from the filter wheel to the next optical element. If that next element is a detector, the image to be detected will be in or out of focus at the detector, depending on which filter is in place, so long as the detector's position is fixed (as it usually is).

This totally unsatisfactory state of affairs has been corrected, in the past, by ensuring that only collimated light passes through the filter wheel. That is, there is no longitudinal chromatic aberration, by definition, when using collimated light. However, this in turn requires care in collimating the light, such as with an excessively large number of collimating lenses on both sides of the filter wheel. For example, two collimating lenses are usually used upstream, and four converging lenses are usually used downstream.

Although such an arrangement has worked very well in the past, there is one drawback—the filter wheel must be between a set of lenses. Hence, it has not been readily feasible to reduce the path length of light as it proceeds from a "source" (usually, the object being illuminated) to the receiving element (usually a detector). That is, the required lenses cannot be crammed into a shorter path length. In contrast, it would be desirable to have a much shorter light path, so as to reduce the size of the reflectometer.

Hence, it has been a long-standing problem, where filter wheels have to be used, that the path length has been excessively long due to the lenses needed both upstream and downstream of the filter wheel.

SUMMARY OF THE INVENTION

We have constructed an optical system, such as in a reflectometer including a filter wheel, and method of use, that solve the aforesaid problem—that is, it allows for a much shorter light path through the filter wheel.

More specifically, in accord with one aspect of the invention, there is provided a filter assembly positioning a plurality of filters in a beam of light, each constructed to pass a different set of wavelengths, comprising:

a) a frame, b) means for mounting the frame for movement with respect to the beam of light, c) and a plurality of filters in the frame, each of the filters having a thickness that is significantly different from that of the other filters, and each filter being constructed to pass a center wavelength of a bandpass that is significantly different from the center wavelength of the others of the filters.

In accord with another aspect of the invention, there is provided a detecting station useful in an analyzer, comprising:

a source of light, a support for locating an object to be illuminated by the source, at least one lens for collecting light reflected by or transmitted through the object, a detector positioned at a predetermined fixed distance from the object support to detect light reflected by or transmitted through said object and collected by the at least one lens, a filter assembly disposed in between the object support and the detector to pass only a limited band of wavelengths of reflected or transmitted light to the detector, the assembly including a plurality of filters each constructed to pass a center wavelength of a bandpass that is significantly different from the center wavelengths of the others of the filters, and means for mounting the assembly to interpose one of the filters at a time to intercept the reflected or transmitted light. This detecting station is improved in that the at least one lens is constructed to deliver non-parallel light beams to and through the filters of the filter assembly, so that filters of differing bandpass construction and substantially the same thickness produce a longitudinal chromatic aberration that alters the angle of light passage through the filter differently depending on the wavelengths of the differing bandpasses, and wherein the filters each have a thickness unique to its different bandpass center wavelength, selected to alter the angle of light beams that pass through the each filter so that they focus on the detector at the fixed distance, regardless of the bandpass of that filter.

In accord with yet another aspect of the invention, there is provided A method of detecting light transmitted through or reflected from a test object on a support, comprising:

a) directing the transmitted or reflected light as a non-collimated beam, b) selecting one of a plurality of filters each having a bandpass and a unique center wavelength of that bandpass, such that each of the filters has a unique thickness peculiar to its center wavelength, c) passing the beam through the selected filter, and d) detecting the passed beam with a detector in the absence of any focusing lenses between the filter and the detector.

As used herein, the center wavelength of a bandpass of a filter is "significantly different" from that of another filter, if it is constructed as to be nominally different from that of the other filters, that is, selected to pass what is considered to be in the trade, a unique center wavelength compared to the other filters. The filter thicknesses are "significantly different", or "unique", if they differ by amounts that are outside normal dimensional tolerances for a nominal thickness. Thus, the "unique" filter thicknesses or "significantly different" filter thicknesses are distinguished from filters intended to have the same nominal thickness, which is the conventional design.

Most preferably, the unique thicknesses bear a predetermined mathematical relationship with the unique center wavelengths, instead of a random or accidental relationship.

Accordingly, it is an advantageous feature of the invention that a reflectometer is provided with plural filters that automatically correct for longitudinal chromatographic aberrations caused by non-collimated light passing through filter bandpasses of differing center wavelength values.

It is a related advantageous feature of the invention that such a reflectometer has a minimum optical path length due to the elimination of the need for a lens(es) between the filter and the detector.

Other advantageous features will become apparent upon reference to the following Detailed Description, when read in light of the attached drawings.

DESCRIPTION OF THE PREFERRED EMBODIMENTS

The invention is hereinafter described in connection with certain preferred embodiments for detecting a preferred test element in a detecting station that comprises a reflectometer using either a filter wheel or a linearly-moved filter frame for positioning any one of several of filters in the light path reflected from the test element. In addition, the invention is applicable regardless of the subject being detected, and regardless of whether light from the subject is reflected or transmitted, or of how the plural filters are mounted or moved into the path of the reflected light, so long as each one of the plural filters has a different center wavelength of its bandpass, and a thickness peculiar to that wavelength so that the reflected beam focuses onto the detector regardless of the center wavelength that comes through the filter.

The preferred test elements detected herein are the slide test elements available under the trademark "VITROS" from Johnson & Johnson Clinical Diagnostics, Inc.

Any glass filter can be used, and since these are conventional, their compositions are not disclosed. Rather, their optical functions, and thicknesses of a preferred set, are recited, inasmuch as any useful filter can be ordered based on these, from conventional sources of filters, such as OCA.

Figure 1:
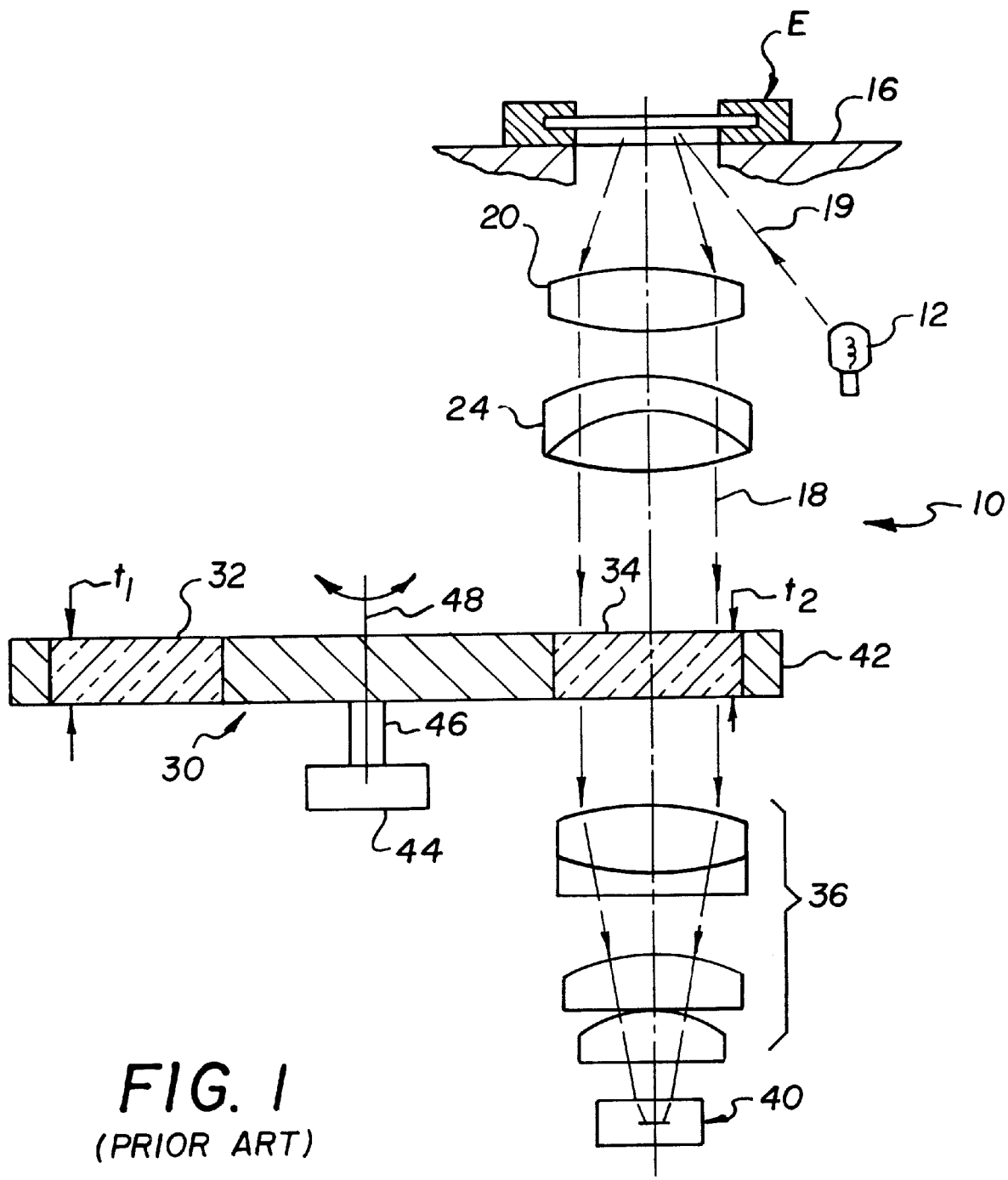
FIG. 1 is a partially schematic sectional view of a portion of a reflectometer, especially the filter wheel portion, constructed in accordance with the prior art.

By way of background, the prior art is illustration FIG. 1. A test element E is detected in a reflectometer 10, comprising a light source 12 shining light 19 onto a platform 16 supporting element E. Reflected rays 18 are collimated by plural lens 20,24, so that a parallel beam passes through a filter 32 or 34 of filter wheel 30, before being refocused by lens assembly 36 and detected by a detector 40. Rotor 42 of wheel 30 is rotated by conventional motor 44 and drive shaft 46. Each filter 32,34, etc. is equidistant from the axis of rotation 48 of shaft 46.

Because filters 32 and 34 (and any others included, not shown) have no particularly selected thickness, i.e., $t_1$ nominally and often actually equaled $t_2$, lenses 36 are needed to correct for the chromatic aberrations introduced by the differing $\lambda_c$ of each filter, where $\lambda_c$ is the center wavelength of the bandpass unique to that filter. Occasionally $t_1$ might not equal $t_2$, but since there was no control over the thicknesses actually used, rays 18 had to be collimated and focussing lenses 36 had to be present.

Figure 2:
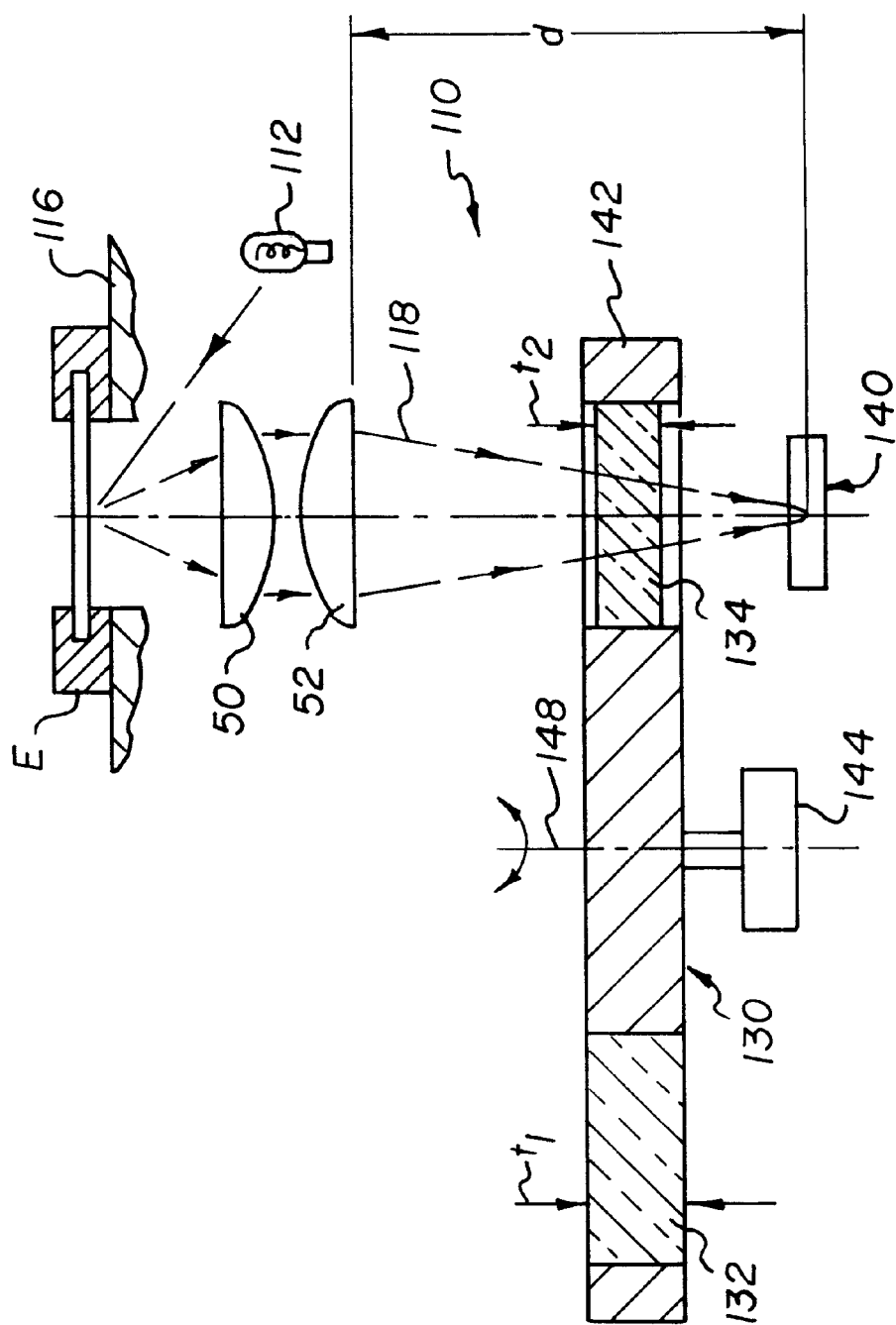
FIG. 2 is a section view similar to that of FIG. 1, except that it illustrates a reflectometer constructed in accordance with the invention.

In contrast, FIG. 2, the reflectometer 110 of the invention has eliminated lenses altogether between wheel 130 and detector 140, and hence has a shorter path length for reflected beam 118—an advantage when space is a premium. Also, lenses 50 and 52 are focusing lenses. The rest of the detecting station 110 remains the same—test element E is supported on platform support 116, to receive illuminating light from source 112, which can be any conventional source, and filter wheel 142 is rotated by motor 144 about axis 148 so that the light is detected by detector 140, which can be conventional detector.

This shorter path length advantage is achieved by making the filters 132,134 (and any others distributed about the circumference of the rotor 142 substantially equidistant from axis 148) each with a significantly different thickness—that is, $t_1 \ne t_2 \ne t_i$ (for i filters). Additionally, the thicknesses are selected peculiar to the center wavelength of the bandpass for that filter, so that the focal distance "d" is the same for all the filters, obviating the need for lenses 36 of the prior art.

The filters are most preferably eight (8) in number, selected to provide for the assays of interest, a preferred selection of significantly different center wavelengths $\lambda_c$ for their bandpass, as noted in Table I below. In addition, each filter has the noted preferred maximum bandpass, although these values are not critical to the mathematical relationship set forth hereinafter, so long as the filters remain narrow bandpass filters.

TABLE I

| Filter Number | $\lambda_c$ (μm) | Maximum Bandpass (nm) |
|---|---|---|
| 1 | 0.340 | 26 |
| 2 | 0.400 | 12 |
| 3 | 0.460 | 22 |
| 4 | 0.540 | 11 |
| 5 | 0.600 | 12 |
| 6 | 0.630 | 13 |
| 7 | 0.670 | 9 |
| 8 | 0.680 | 13 |

Given these values for $\lambda_c$, the thicknesses for each filter are selected in accordance with the following predetermined formula:

$$t = \frac{S \cdot \sqrt{\frac{B_1 \lambda_c^2}{(\lambda_c^2 - C_1)} + \frac{B_2 \lambda_c^2}{(\lambda_c^2 - C_2)} + \frac{B_3 \lambda_c^2}{(\lambda_c^2 - C_3)} + 1}}{\left( \sqrt{\frac{B_1 \lambda_c^2}{(\lambda_c^2 - C_1)} + \frac{B_2 \lambda_c^2}{(\lambda_c^2 - C_2)} + \frac{B_3 \lambda_c^2}{(\lambda_c^2 - C_3)} + 1} \right) - 1}$$

wherein t=thickness of the filter in mm, S=change in focal length in mm due to the presence of the filter (a constant value, $\lambda_c$=the center wavelength in microns of the bandbass of the filter, and $B_1$, $B_2$, $B_3$, $C_1$, $C_2$, and $C_3$ are constants of the Sellmeier Dispersion Formula, available from glass manufacturers.

The above equation is derived from the Sellmeier Dispersion Formula, and Snell's law simplified for use with small angles of incidence, easily S=(t/n)(n−1), wherein S+t are as defined above, and n is the index of refraction. Based on this equation, the filters have the preferred and unique thicknesses, for their given $\lambda_c$, set forth in Table II:

TABLE II

| Filter Number | Thickness (in mm) |
|---|---|
| 1 | 6.096 |
| 2 | 7.093 |
| 3 | 7.296 |
| 4 | 7.276 |
| 5 | 7.194 |
| 6 | 7.145 |
| 7 | 7.075 |
| 8 | 7.057 |

(The optical assembly of FIG. 2 with these filters is adjusted to provide an F number of 3.8.)

It will be appreciated that, for other values of $\lambda_c$ and "d", thicknesses different from those of Table I can be selected.

In use, wheel 142 is rotated so that only one or another of the plural filters therein (e.g., filter number 1, 2, . . . 8) is selected at any one time to intercept beam 118 that is converging through the filter. The selection of course is made based upon the detectable wavelength that is optimized for a given test element E, as is well-known.

Figure 3:
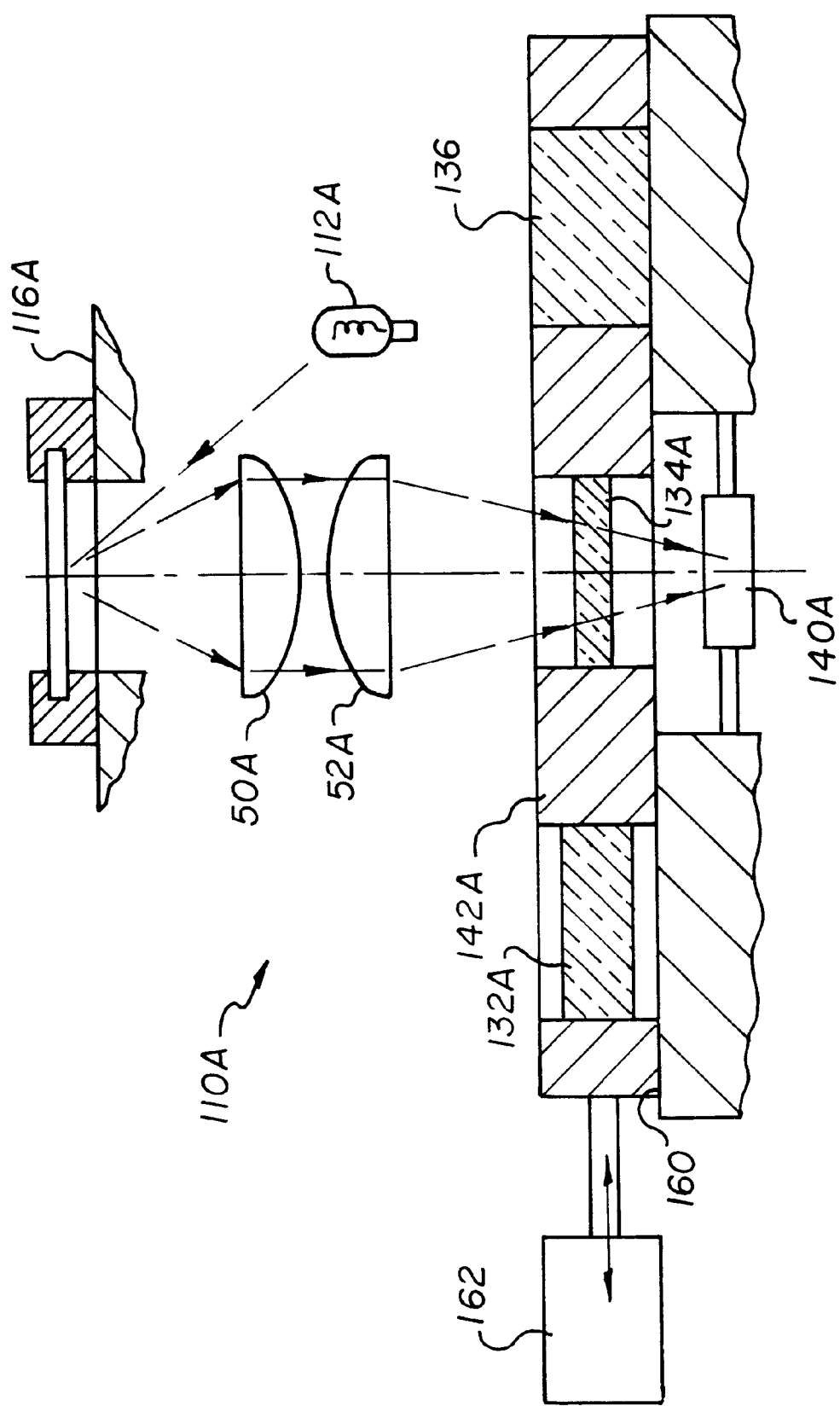
FIG. 3 is a section view similar to that of FIG. 2, but showing an alternate embodiment of the invention.

It is not necessary that the detecting station use a filter wheel to move the various filters into position. Instead, a linearly-moveable frame can be used that is reciprocated back and forth, FIG. 3. Parts similar to those described above bear the same reference numeral, to which the distinguishing suffix "A" is appended.

Thus, detecting station 110A uses a platform support 116A, light source 112A, focusing lenses 50A and 52A, detector 140A, and plural filters 132A,134A, etc., each with a unique center wavelength and thickness, all as described above for the embodiment of FIG. 2. What is different, however, is that filters 132A,134A, etc. are mounted in a frame 142A that is slideable over support 160, as reciprocatingly driven by linear actuator 162.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a detecting station useful in an analyzer, comprising:

a source of light, a support for locating an object to be illuminated by the source, at least one lens for collecting light reflected by or transmitted through said object, a detector positioned at a predetermined fixed distance from said object support to detect light reflected by or transmitted through said object and collected by said at least one lens, a filter assembly disposed in between said object support and said detector to pass only a limited band of wavelengths of reflected or transmitted light to said detector, said assembly including a plurality of filters each constructed to pass a center wavelength of a bandpass that is significantly different from the center wavelengths of the others of said filters, and means for mounting said assembly to interpose one of said filters at a time to intercept said reflected or transmitted light;

the improvement wherein said at least one lens is constructed to deliver non-parallel light beams to and through said filters of said filter assembly, so that if filters were to be used having differing bandpass construction and substantially the same thickness, a longitudinal chromatic aberration would be produced that alters the angle of light passage through the filter differently depending on the wavelengths of said differing bandpasses, and wherein said filters each have a fixed thickness unique to its different bandpass center wavelength, selected to alter the angle of light beams that pass through said each filter so that they focus on said detector at said fixed distance, regardless of the bandpass of that filter.

2. A detecting station as defined in claim 1, wherein said unique thicknesses are selected in accordance with a predetermined mathematical relationship to said significantly differing center wavelength.

3. A detecting station as defined in claim 1 or 2, wherein said selected thicknesses obey the mathematical relationship of the following equation:

$$t = \frac{S \cdot \sqrt{\frac{B_1 \lambda_C^2}{(\lambda_C^2 - C_1)} + \frac{B_2 \lambda_C^2}{(\lambda_C^2 - C_2)} + \frac{B_3 \lambda_C^2}{(\lambda_C^2 - C_3)} + 1}}{\left(\sqrt{\frac{B_1 \lambda_C^2}{(\lambda_C^2 - C_1)} + \frac{B_2 \lambda_C^2}{(\lambda_C^2 - C_2)} + \frac{B_3 \lambda_C^2}{(\lambda_C^2 - C_3)} + 1}\right) - 1}$$

wherein t=thickness of the filter in mm, S=the change in focal length due to the presence of the filter, $\lambda_c$=the center wavelength in microns of the bandbass of the filter, and $B_1$, $B_2$, $B_3$, $C_1$, $C_2$, and $C_3$ are constants of the Sellmeier Dispersion Formula.

4. A detecting station as defined in claim 1 or 2, wherein said assembly comprises a rotor, and said mounting means comprise a drive shaft and a motor for rotating said rotor about an axis of rotation.

5. A detecting station as defined in claim 3, wherein said plural filters are disposed around the circumference of said rotor substantially at an equal distance from said axis of rotation.

6. A detecting station as defined in claim 1 or 2, wherein said filters are selected to provide the following center wavelengths of the bandpass:

| Filter # | $\lambda_c$ ($\mu$m) |
| --- | --- |
| 1 | 0.340 |
| 2 | 0.400 |
| 3 | 0.460 |
| 4 | 0.540 |
| 5 | 0.600 |
| 6 | 0.630 |
| 7 | 0.670 |
| 8 | 0.680. |

7. A detecting station as defined in claim 1 or 2, wherein said at least one lens is a focussing lens.

8. A method of detecting light transmitted through or reflected from a test object on a support, comprising:

a) directing said transmitted or reflected light as a non-collimated beam, b) selecting one of a plurality of filters each having a bandpass and a unique center wavelength of that bandpass, such that each of said filters has a unique fixed thickness peculiar to its center wavelength, c) passing said beam through said selected filter, and d) detecting said passed beam which is focused on a detector that is it a predetermined fixed distance from said test object in the absence of any focusing lenses between said filter and said detector.

9. A detecting method as defined in claim 8, wherein said unique thickness is selected in accordance with a predetermined mathematical relationship to said unique center wavelength.

10. A detecting method as defined in claim 8 or 9, wherein said unique center wavelength and said unique thickness are related in accordance with the following equation:

$$t = \frac{S \cdot \sqrt{\frac{B_1 \lambda_C^2}{(\lambda_C^2 - C_1)} + \frac{B_2 \lambda_C^2}{(\lambda_C^2 - C_2)} + \frac{B_3 \lambda_C^2}{(\lambda_C^2 - C_3)} + 1}}{\left(\sqrt{\frac{B_1 \lambda_C^2}{(\lambda_C^2 - C_1)} + \frac{B_2 \lambda_C^2}{(\lambda_C^2 - C_2)} + \frac{B_3 \lambda_C^2}{(\lambda_C^2 - C_3)} + 1}\right) - 1}$$

wherein t=thickness of the filter in mm, S=the change in focal length due to the presence of the filter, $\lambda_c$=the center wavelength in microns of the bandbass of the filter, and $B_1$, $B_2$, $B_3$, $C_1$, $C_2$, and $C_3$ are constants of the Sellmeier Dispersion Formula.

\* \* \* \* \*